United States Patent
Wakabayashi et al.

(10) Patent No.: US 10,568,509 B2
(45) Date of Patent: Feb. 25, 2020

(54) MEDICAL DEVICE SYSTEM AND MEDICAL DEVICE

(71) Applicant: NIHON KOHDEN CORPORATION, Tokyo (JP)

(72) Inventors: Tsutomu Wakabayashi, Tokyo (JP); Ko Kamada, Tokyo (JP); Takayuki Tanaka, Tokyo (JP); Yuko Ishinabe, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 151 days.

(21) Appl. No.: 14/831,222

(22) Filed: Aug. 20, 2015

(65) Prior Publication Data
US 2016/0058285 A1 Mar. 3, 2016

(30) Foreign Application Priority Data

Aug. 29, 2014 (JP) .................................. 2014-174783

(51) Int. Cl.
*A61B 5/0215* (2006.01)
*A61B 5/00* (2006.01)
(Continued)

(52) U.S. Cl.
CPC ........ *A61B 5/0002* (2013.01); *G06F 19/3418* (2013.01); *G16H 10/60* (2018.01); *G16H 40/63* (2018.01)

(58) Field of Classification Search
CPC ..... A61B 5/021; A61B 5/0002; A61B 5/0015; A61B 5/02125; A61B 5/0255; G06F 19/3412; G06F 21/445; G06F 21/46
See application file for complete search history.

(56) References Cited

U.S. PATENT DOCUMENTS 5,423,325 A * 6/1995 Burton ................. A61B 5/0436
                                                         600/515
5,748,103 A * 5/1998 Flach .................. A61B 5/0006
                                                         340/870.07
(Continued)

FOREIGN PATENT DOCUMENTS

CN         1910610 A     2/2007
CN        102989054 A    3/2013
(Continued)

OTHER PUBLICATIONS

"Monitor (Medizin)" Wikipedia, retrieved Mar. 28, 2013.
(Continued)

*Primary Examiner* — Hai Phan
*Assistant Examiner* — Son M Tang
(74) *Attorney, Agent, or Firm* — Pearne & Gordon LLP (57) ABSTRACT

A medical device system includes a first medical device and a second medical device. The first medical devices includes a first measuring unit that acquires measurement data of vital signs of a patient and a first communication unit that transmits the measurement data acquired by the first measuring unit to the second medical device. The second medical device includes a second communication unit that receives the measurement data from the first communication unit. The first and second medical devices are configured so that if certification processing succeeds, the measurement data is permitted to be used in the second medical device.

7 Claims, 8 Drawing Sheets

(51) Int. Cl.
*G16H 40/63* (2018.01)
*G16H 10/60* (2018.01)
*G06F 19/00* (2018.01)

(56) References Cited

U.S. PATENT DOCUMENTS

| | | | | |
|---|---|---|---|---|
| 5,842,980 A * | 12/1998 | Tsuda | A61B 1/018 | 600/410 |
| 6,041,257 A * | 3/2000 | MacDuff | G01D 3/02 | 607/5 |
| 6,057,758 A * | 5/2000 | Dempsey | A61N 1/08 | 340/539.12 |
| 6,141,584 A * | 10/2000 | Rockwell | A61N 1/39 | 128/903 |
| 6,668,196 B1 * | 12/2003 | Villegas | A61M 5/172 | 607/60 |
| 6,990,371 B2 * | 1/2006 | Powers | A61N 1/3925 | 600/510 |
| 7,047,065 B2 * | 5/2006 | Kalgren | A61B 5/0006 | 600/510 |
| 7,640,055 B2 * | 12/2009 | Geva | A61B 5/00 | 600/544 |
| 7,860,456 B2 * | 12/2010 | Kim | H04L 63/0869 | 455/41.2 |
| 8,090,409 B2 | 1/2012 | Brown et al. | | |
| 8,135,462 B2 * | 3/2012 | Owen | A61B 5/02416 | 600/310 |
| 8,391,975 B2 * | 3/2013 | Corbucci | A61B 5/0006 | 607/11 |
| 8,533,475 B2 * | 9/2013 | Frikart | G06F 19/3406 | 455/41.2 |
| 8,548,584 B2 * | 10/2013 | Jorgenson | A61N 1/37247 | 607/10 |
| 8,700,128 B2 * | 4/2014 | Assis | A61B 6/12 | 382/128 |
| 8,753,274 B2 * | 6/2014 | Ziv | A61B 5/0002 | 600/301 |
| 8,907,782 B2 * | 12/2014 | Baker | G06F 19/322 | 340/539.12 |
| 8,957,777 B2 * | 2/2015 | Baker | A61B 5/0024 | 340/538.15 |
| 8,978,117 B2 * | 3/2015 | Bentley | G06F 21/32 | 455/411 |
| 9,070,280 B2 * | 6/2015 | Baker | G08C 17/02 | |
| 9,233,255 B2 * | 1/2016 | Powers | A61B 5/0006 | |
| 9,455,979 B2 * | 9/2016 | Blanke | H04L 9/3263 | |
| 9,486,571 B2 * | 11/2016 | Rosinko | A61M 5/14244 | |
| 9,514,276 B2 * | 12/2016 | Daynes | A61N 1/3925 | |
| 9,532,225 B2 * | 12/2016 | MacKenzie | H04W 12/08 | |
| 9,577,999 B1 * | 2/2017 | Lindemann | H04L 29/06 | |
| 9,737,656 B2 * | 8/2017 | Rosinko | A61M 5/14244 | |
| 9,833,632 B2 * | 12/2017 | Herleikson | A61N 1/3987 | |
| 9,907,947 B2 * | 3/2018 | Geheb | A61N 1/3625 | |
| 2002/0152034 A1 * | 10/2002 | Kondo | G06K 9/00 | 702/19 |
| 2004/0127774 A1 * | 7/2004 | Moore | A61N 1/3925 | 600/300 |
| 2004/0204743 A1 * | 10/2004 | McGrath | A61N 1/08 | 607/5 |
| 2005/0097191 A1 * | 5/2005 | Yamaki | G06F 19/3406 | 709/219 |
| 2005/0119535 A1 | 6/2005 | Yanagihara et al. | | |
| 2006/0047192 A1 * | 3/2006 | Hellwig | G06F 19/3468 | 600/365 |
| 2006/0149597 A1 * | 7/2006 | Powell | G01D 21/00 | 705/2 |
| 2006/0200009 A1 | 9/2006 | Wekell et al. | | |
| 2007/0003061 A1 * | 1/2007 | Jung | H04L 63/061 | 380/270 |
| 2007/0073347 A1 | 3/2007 | Corbucci | | |
| 2008/0191839 A1 | 8/2008 | Sato | | |
| 2008/0255625 A1 | 10/2008 | Powers | | |
| 2009/0096573 A1 * | 4/2009 | Graessley | H04W 12/04 | 340/5.8 |
| 2010/0045425 A1 * | 2/2010 | Chivallier | A61B 5/0002 | 340/5.8 |
| 2010/0115279 A1 | 5/2010 | Frikart et al. | | |
| 2010/0241857 A1 | 9/2010 | Okude et al. | | |
| 2011/0018754 A1 | 1/2011 | Tojima et al. | | |
| 2011/0320131 A1 | 12/2011 | Hibino et al. | | |
| 2012/0003933 A1 * | 1/2012 | Baker | G06F 19/3412 | 455/41.2 |
| 2012/0046562 A1 * | 2/2012 | Powers | A61B 5/042 | 600/509 |
| 2012/0182301 A1 * | 7/2012 | Wenholz | A61B 5/044 | 345/440.1 |
| 2013/0271470 A1 * | 10/2013 | Moore | G16H 10/60 | 345/440.1 |
| 2014/0181183 A1 | 6/2014 | Houjou et al. | | |
| 2014/0280581 A1 * | 9/2014 | Hernandez | H04L 29/08072 | 709/204 |

FOREIGN PATENT DOCUMENTS

| | | |
|---|---|---|
| EP | 2 001 188 A1 | 12/2008 |
| JP | 2003-271737 A | 9/2003 |
| JP | 2003-319913 A | 11/2003 |
| JP | 2005-152401 A | 6/2005 |
| JP | 2009-508618 A | 3/2009 |
| JP | 2009-260934 A | 11/2009 |
| JP | 2012-008931 A | 1/2012 |
| JP | 2012-235874 A | 12/2012 |
| JP | 2014-096054 A | 5/2014 |
| JP | 2014-140145 A | 7/2014 |
| WO | 2009-063947 A1 | 5/2009 |
| WO | 2014-097117 A2 | 6/2014 |

OTHER PUBLICATIONS

European Search Report for Application No. 15 18 1786 dated Feb. 24, 2016.
Japanese Office Action issued in Patent Application No. JP-2014-174783 dated Jan. 19, 2018.
Japanese Office Action issued in Patent Application No. JP-2014-174783 dated Mar. 7, 2018.
European Office Action issued in Patent Application No. EP-15 181 786.3 dated Aug. 10, 2018.
Japanese Decision to Decline the Amendment issued in Japanese Patent Application No. JP 2014-174783 dated Sep. 19, 2018.
Japanese Office Action issued in Japanese Patent Application No. JP 2014-174783 dated Sep. 19, 2018.
Chinese Office action issued in Chinese Patent Application No. 201510519875 dated Jan. 4, 2019.
Chinese Office action issued in Chinese Patent Application No. 201510519875 dated Jun. 3, 2019.
Summons to attend oral proceedings issued in Patent Application No. EP 15 181 786 dated Jun. 12, 2019.
Chinese Office action issued in Chinese Patent Application No. 201510519875 dated Sep. 9, 2019.

* cited by examiner

MEDICAL DEVICE SYSTEM AND MEDICAL DEVICE

CROSS REFERENCE TO RELATED APPLICATION

This application is based on Japanese Patent Applications No. 2014-174783 filed on Aug. 29, 2014, the contents of which are incorporated herein by reference.

BACKGROUND

The present invention relates to a medical device system and a medical device, in particular, to a medical device system and a medical device, which sends and receives measurement data of vital signs using a communication function.

Recently, networking of medical devices is progressed. As a result, an ability of transmitting and receiving data between medical devices is also enhanced. Such a data communication between medical devices needs to be smoothly performed and also to be correctly performed so that confusion in information of patients is not occurred.

Now, techniques related to data transmission and reception between medical devices or between a medical device and a medical system server will be described. JP-A-2009-508618 discloses a system in which ECG (Electrocardiogram) is transmitted from a first medical monitoring device (such as AED) to a second device (such as a defibrillator for an emergency rescue team).

Also, JP-A-2005-152401 discloses a system in which a medical measuring device transmits measurement data in a wireless manner. The medical measuring device decides whether or not an opposing device receives the measurement data by ACK and retransmits the measurement data if it is decided that the measurement data is not received.

JP-A-2012-235874 discloses one aspect of AED (Automated External Defibrillator) having a communication function. The AED includes a sensor for measuring vital signs (such as body temperature). Also, the AED transmits information measured by the sensor to a server of a medical institution.

As described above, there is a case where data measured by a certain medical device is desired to be transmitted to other medical devices. For example, it is preferable that measurement data acquired by a defibrillator equipped in an ambulance can be transmitted to a patient monitor of a medical institution and the like. As a result, doctors or nurses can also refer to various measurement data before a patient is connected to the patient monitor.

At this time, in order to avoid confusion between patients in transferring of data, transmission and reception of correct measurement data between both devices have to be ensured. For example, a situation where the patient monitor connected to a certain patient is handling measurement data of another patient has to be avoided.

However, in the related art including JP-A-2009-508618, JP-A-2005-152401 and JP-A-2012-235874, there is no suggestion and mention on a structure and a scheme in which measurement data can be transmitted and received between correct devices.

Accordingly, the present invention has been made in view of the above problem, and a primary object thereof is to provide a medical device system and a medical device, in which a transmission and reception of measurement data can be performed between correct devices.

SUMMARY

According to an aspect of the invention, a medical device system includes a first medical device and a second medical device. The first medical devices includes a first measuring unit that acquires measurement data of vital signs of a patient and a first communication unit that transmits the measurement data acquired by the first measuring unit to the second medical device. The second medical device includes a second communication unit that receives the measurement data from the first communication unit. The first and second medical devices are configured so that if certification processing succeeds, the measurement data is permitted to be used in the second medical device.

DETAILED DESCRIPTION OF EMBODIMENTS

Embodiment 1

Figure 1:
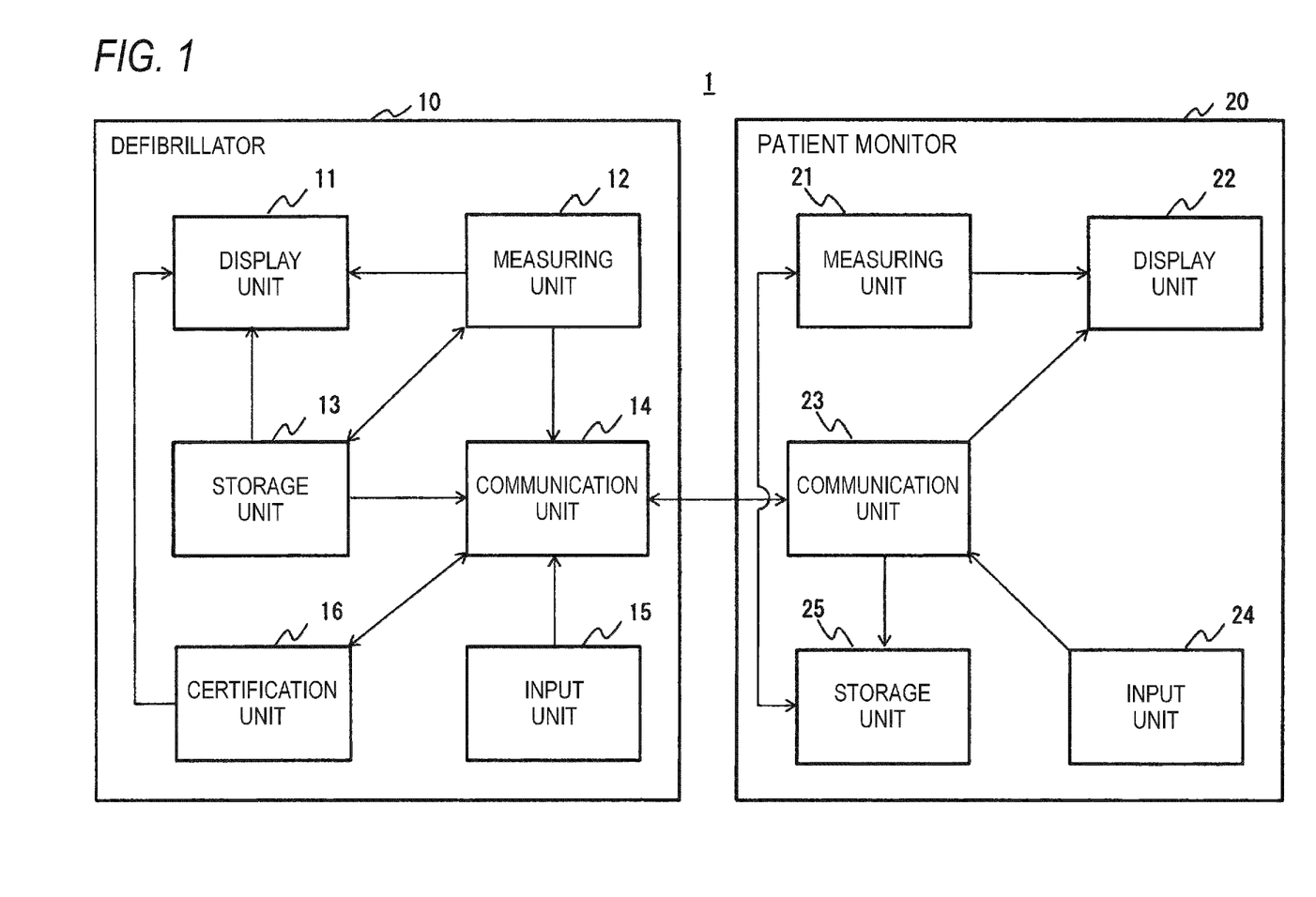
FIG. 1 is a block diagram showing a configuration of a medical device system according to an embodiment 1.

Embodiments of the present invention will be now described with reference to the accompanying drawings. FIG. 1 is a block diagram showing a configuration of a medical device system according to the embodiment 1. The medical device system 1 includes a defibrillator 10 (first medical device) and a patient monitor 20 (second medical device). The defibrillator 10 and the patient monitor 20 are one aspect of medical devices for measuring vital signs (e.g., body temperature, blood pressure, electrocardiogram, SpO2 and the like) of a patient.

The defibrillator 10 is equipped in an ambulance, for example. The defibrillator 10 is configured to acquire and display measurement data (such as electrocardiogram) of various vital signs as well as to perform defibrillating (electric shock) or pacing. The defibrillator 10 includes a display unit 11 (first display unit), a measuring unit 12 (first measuring unit), a storage unit 13, a communication unit 14 (first communication unit), an input unit 15 and a certification unit 16. In addition to such processing units, the defibrillator 10 has a capacitor for charging energy, a control unit including a CPU (Central Processing Unit), connectors for electrodes and the like.

The defibrillator 10 is connected to a skin surface of a patient via electrodes (not shown). Similarly, the patient monitor 20 is connected to the skin surface of the patient via electrodes (not shown). The patient monitor 20 is configured to measure parameters of various vital signs from electrical signals acquired through the electrodes.

In the following description, a case where a defibrillator 10 in an ambulance or the like is removed from a patient, to whom the defibrillator 10 has been mounted, and then a patient monitor 20 is mounted to the patient will be described as an example. At this time, it is assumed that measurement data acquired by the defibrillator 10 is used in the patient monitor 20.

The display unit 11 is a liquid crystal display or the like provided on a surface of a housing of the defibrillator 10. The input unit 15 is various input interfaces (knobs, buttons and the like provided on a body of the housing) for operating the defibrillator 10. Alternatively, the display unit 11 and the input unit 15 may be an integrated configuration, such as a touch display. A user inputs certification information (input password) through the input unit 15.

The measuring unit 12 acquires measurement data (body temperature, blood pressure, electrocardiogram, SpO2 and the like) of various vital signs received from electrodes not shown. For example, the measuring unit 12 acquires electrocardiogram waveforms by filtering and amplifying electrocardiogram signals received from the electrodes not shown. The measuring unit 12 stores the measurement data of the vital signs (e.g., electrocardiogram waveforms) to the storage unit 13 and also displays the measurement data on the display unit 11.

The storage unit 13 is a secondary storage device such as a hard disk. The storage unit 13 is configured to store therein various programs, audio data and measurement data (such as electrocardiogram) measured by the measuring unit 12. A part of the storage unit 13 may be configured to be removable from the defibrillator 10, such as a USB (Universal Serial Bus) memory.

The certification unit 16 creates a password (in the following description, also referred to as a required password) which must be inputted through the input unit 15 of the defibrillator 10. The certification unit 16 displays the created required password on the display unit 11 or a display unit 22 (display) of the patient monitor 20. Also, the certification unit 16 decides whether or not certification information (input password) inputted through the input unit 15 corresponds to the required password. The certification unit 16 decides that certification succeeds if the input password corresponds to the required password. When certification succeeds, the measurement data is allowed to be used in the patient monitor 20. Herein, the phrase "the input password corresponds to the required password" preferably means that both are identical, but not required to be perfectly identical. For example, the concept encompasses a relationship that both passwords correspond to each other in accordance with a predetermined rule as in the Cesar's code.

The communication unit 14 is a communication interface for transmitting the measurement data to the patient monitor 20. The communication unit 14 is an interface equipped with, for example, Bluetooth (registered trademark). The communication unit 14 transmits the measurement data, which are stored in the storage unit 13, to the patient monitor 20. Upon transmitting, the communication unit 14 performs such processing by referring to whether certification processing succeeds. Details of the certification processing will be described below with reference to FIGS. 2 and 4.

Next, a configuration of the patient monitor 20 will be described. The patient monitor 20 includes a measuring unit 21 (second measuring unit), a display unit 22 (second display unit), a communication unit 23 (second communication unit), an input unit 24 and a storage unit 25.

The measuring unit 21 acquires measurement data (body temperature, blood pressure, electrocardiogram, SpO2 and the like) of various vital signs based on electrical signals from electrodes not shown. The measuring unit 21 stores the acquired measurement data to the storage unit 25. Also, the measuring unit 21 displays the acquired measurement data to the display unit 22.

The display unit 22 is a liquid crystal display or the like provided on the patient monitor 20. Alternatively, the display unit 22 may be combined with an input unit as in a touch display.

The storage unit 25 is configured to store therein various programs for operating the patient monitor 20, audio programs, various vital sign data acquired by the measuring unit 21, and the like. A part of the storage unit 25 may be configured to be removable from the patient monitor 20, such as a USB (Universal Serial Bus) memory.

The communication unit 23 is a communication interface for transmitting and receiving data to and from the defibrillator 10. The communication unit 23 is an interface equipped with, for example, Bluetooth (registered trademark) which is a short-distance wireless communication standard.

The input unit 24 is an input interface provided on the patient monitor 20 and, for example, is buttons, a touch display and the like.

The input password and the required password are not necessary to be letters (such as alphabet), and thus may be combinations of alphabet and numbers, ones including symbols (such as quadrangles, triangles and circles) and the like.

Next, details of certification processing between the defibrillator 10 and the patient monitor 20 will be described with reference to FIGS. 2 and 3.

[First Certification Processing Example]

Figure 2:
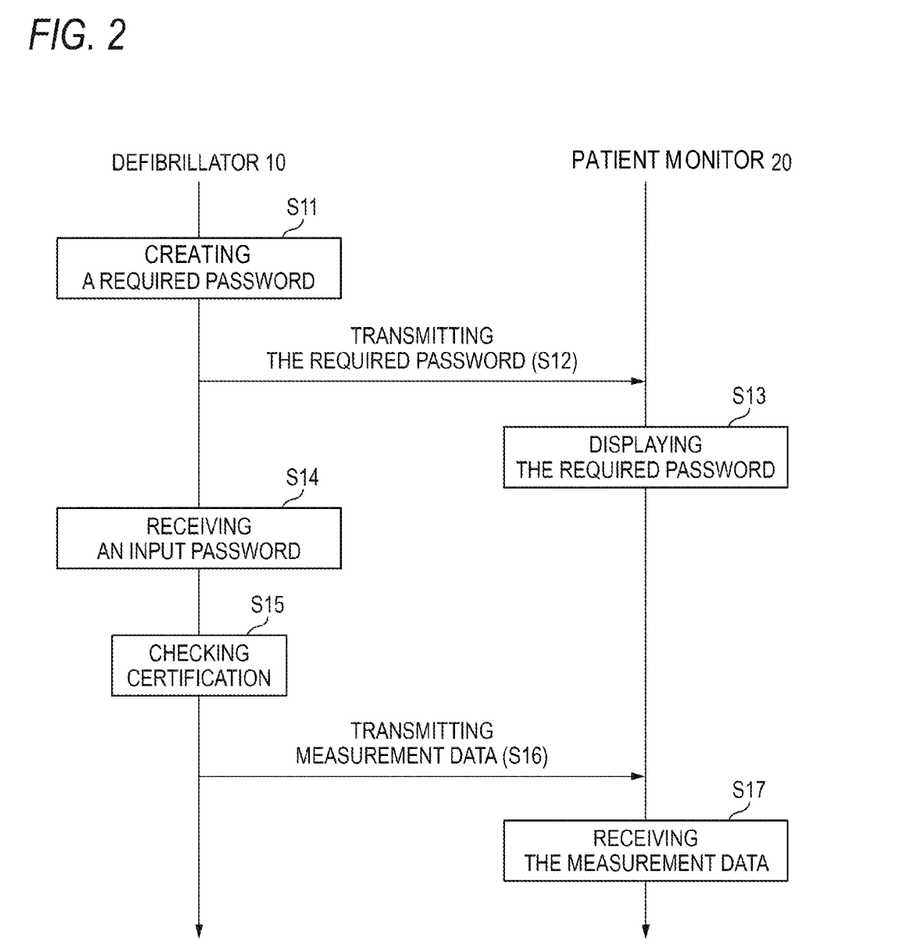
FIG. 2 is a timing chart showing a first certification processing example between a defibrillator 10 and a patient monitor 20 according to the present invention.

FIG. 2 is a timing chart showing a first certification processing example between the defibrillator 10 and the patient monitor 20 according to the present embodiment.

The certification unit 16 in the defibrillator 10 creates a required password (S11). In this case, preferably, creation of the required password is performed by creating a random letter string. Herein, as the required password, a letter string in which a type of the input unit 15 (such as the number of input buttons) is taken into account is employed. The certification unit 16 transmits the created required password to the patient monitor 20 through the communication unit 14 (S12). The display unit 22 in the patient monitor 20 displays the received required password (S13). A user (e.g., a nurse) inputs a password through the input unit 15 of the defibrillator 10, while referring to the required password displayed on the patient monitor 20 (S14). The certification unit 16 decides whether or not the input password corresponds to the required password and then decides that certification succeeds if the input password corresponds to the required password (S15). When certification succeeds, the communication unit 14 transmits measurement data to the patient monitor 20 (S16). The communication unit 23 displays the received measurement data on the display unit 22 (S17).

Figure 3:
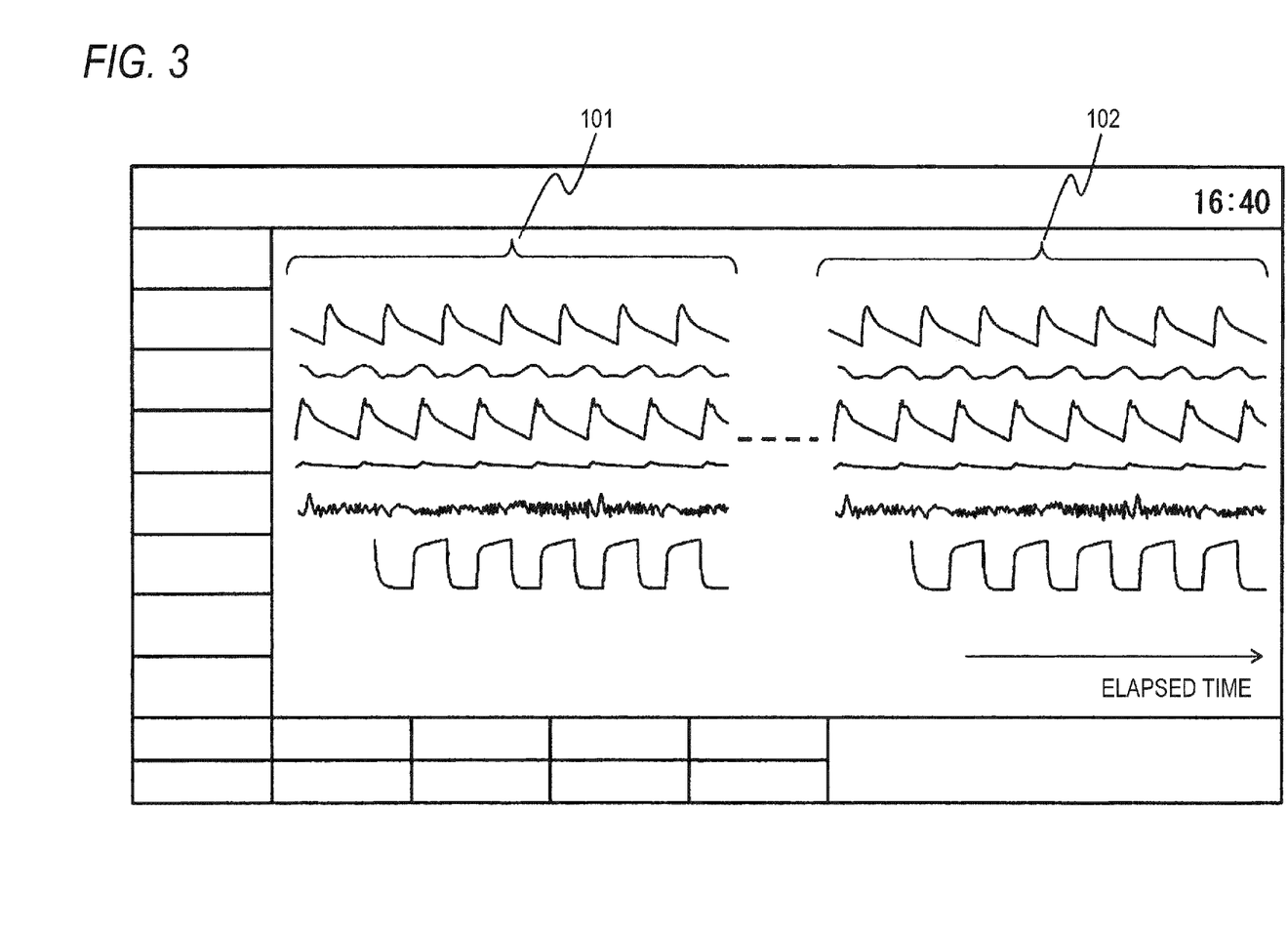
FIG. 3 is a view showing an example of a display screen of a display unit 22 according to the embodiment 1.

FIG. 3 is an example of a display screen of the display unit 22 after the measurement data is received. The display screen is configured to array and display various measurement data 101 acquired at the defibrillator 10 and various measurement data 102 acquired at the patient monitor in time series. Herein, the term measurement data generally means data in which time information and numerical information are paired. Accordingly, as shown in FIG. 3, the patient monitor 20 is preferably configured to array and display the measurement data 101 acquired at the defibrillator 10 and the measurement data 102 acquired at the patient monitor 20 in time series.

[Second Certification Processing Example]

Figure 4:
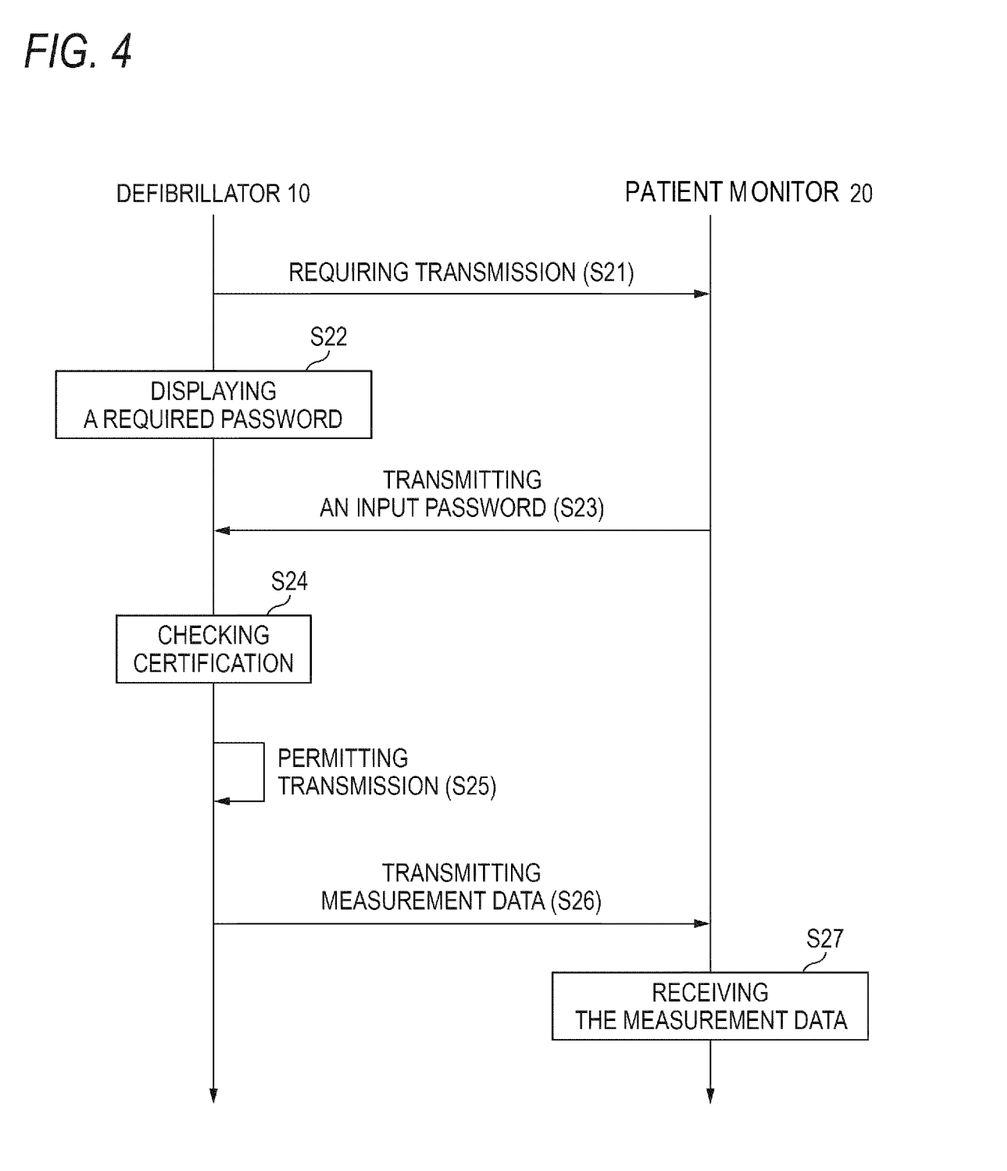
FIG. 4 is a timing chart showing a second certification processing example between the defibrillator 10 and the patient monitor 20 according to the present invention.

The second certification processing example will be now described with reference to FIG. 4. In response to a certain trigger (e.g., a transmission demand by operation of the input unit 15), the communication unit 14 in the defibrillator 10 transmits a transmission demand of measurement data to the patient monitor 20 (S21). Then, the certification unit 16 in the defibrillator 10 creates a required password and displays the required password on the display unit 11 (S22).

A user (e.g., a nurse), who is to perform operation for data transfer, inputs a password corresponding to the required password through the input unit 24 while referring to the required password displayed on the display unit 11 (S23). Then, the communication unit 23 transmits the input password to the defibrillator 10 (S23).

The communication unit 14 of the defibrillator 10 receives the input password (S23). The certification unit 16 decides whether or not the received input password corresponds to the required password (S24). When two passwords do not correspond to each other, the communication unit 14 does not perform transmission of measurement data. When two passwords correspond to each other, the certification unit 16 decides that transmission of the measurement data acquired by the measuring unit 12 is permitted. When transmission of the measurement data is permitted, the communication unit 14 transmits the measurement data acquired by the measuring unit 12 to the patient monitor 20 (S26).

The communication unit 23 receives the measurement data from the defibrillator 10 (S26). Then, the communication unit 23 displays the received measurement data on the display unit 22 (S27).

[Third Certification Processing Example]

Figure 5:
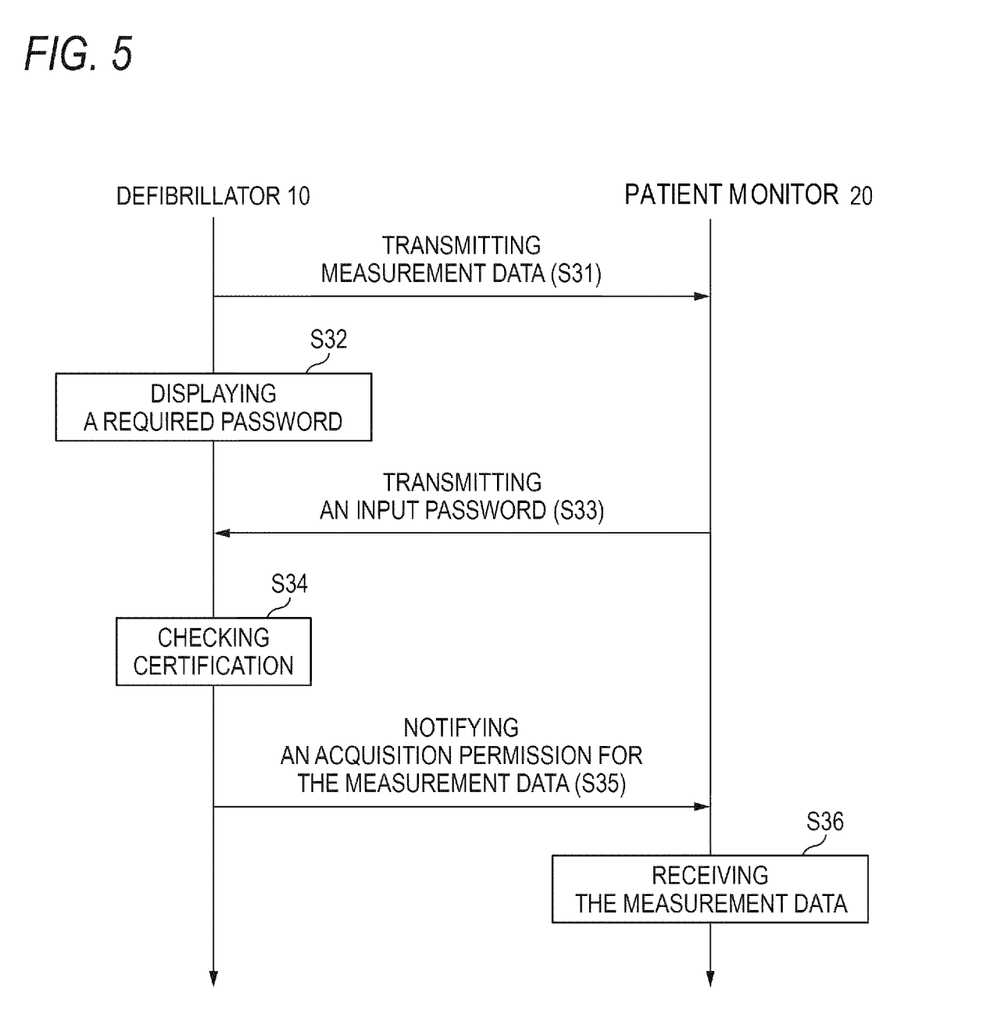
FIG. 5 is a timing chart showing a third certification processing example between the defibrillator 10 and the patient monitor 20 according to the present invention.

The third certification processing example will be now described with reference to FIG. 5. On the basis of a certain trigger (e.g., pressing of a transmission button), the communication unit 14 of the defibrillator 10 transmits measurement data to the patient monitor 20 (S31). Also, the certification unit 16 of the defibrillator 10 creates a required password and displays the required password on the display unit 11 (S32).

A user (e.g., a nurse), who is to perform operation for data transfer, inputs a password corresponding to the required password through the input unit 24 while referring to the required password displayed on the display unit 11 (S33). Then, the communication unit 23 transmits the input password to the defibrillator 10 (S33).

The communication unit 14 of the defibrillator 10 receives the input password (S33). The certification unit 16 decides whether or not the received input password corresponds to the required password (S34). If two passwords do not correspond to each other, the communication unit 14 does not transmit an acquisition permission notification for the measurement data. On the other hand, if two passwords correspond to each other, the communication unit 14 transmits the acquisition permission notification for the measurement data (S35).

When receiving the acquisition permission notification for the measurement data, the communication unit 23 displays the measurement data received at S31 on the display unit 22 (S36). Meanwhile, the patient monitor 20 deletes the measurement data received from the defibrillator 10, if a predetermined period of time is elapsed without receiving the acquisition permission notification for the measurement data after transmitting the input password.

Embodiment 2

Figure 6:
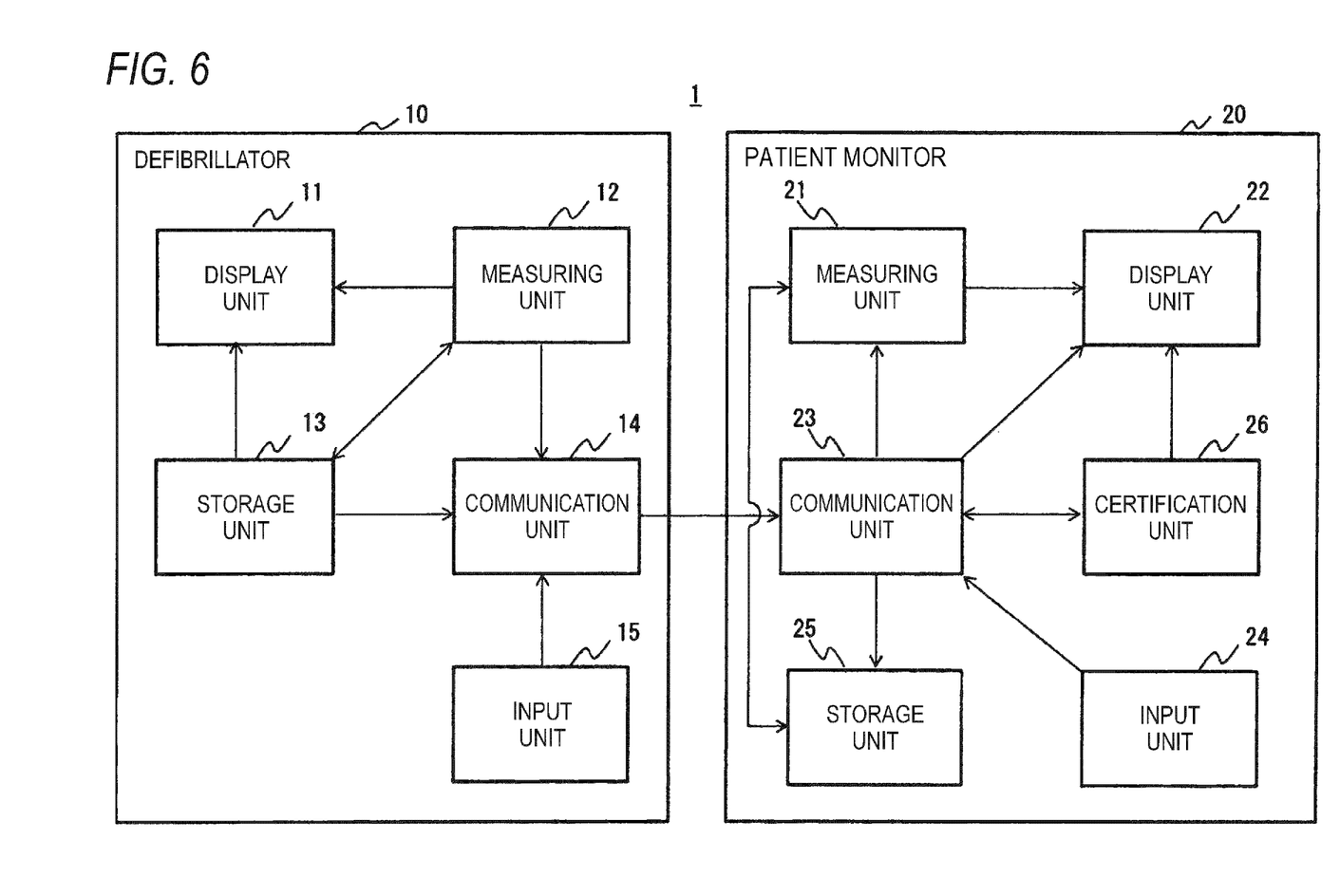
FIG. 6 is a block diagram showing a configuration of a medical device system according to an embodiment 2.

Next, a configuration of a medical device system 1 according to the embodiment 2 will be described. The medical device system 1 according to the present embodiment is different from the embodiment 1, in that certification processing is performed on a receiving-side device. Hereinafter, differences from the embodiment 1 will be mainly described. Meanwhile, processing unit designated by the same terms and reference numerals as those of the embodiment 1 in the drawings are regarded as performing the same processing as those of the embodiment 1, if not specifically mentioned.

FIG. 6 is a block diagram showing a configuration of the medical device system 1 according to the present embodiment. A defibrillator 10 according to the present embodiment has a configuration in which the certification unit 16 is not equipped therein, as compared to the configuration shown in FIG. 1. A patient monitor 20 is different from the configuration of FIG. 1 in that a certification unit 26 is equipped therein.

Operations using the medical device system 1 according to the present embodiment will be schematically described. The patient monitor 20 receives an input password from the defibrillator 10. The patient monitor 20 performs certification processing using the received input password and a required password, and if the certification succeeds, measurement data measured by the defibrillator 10 is permitted to be used in the patient monitor 20. Hereinafter, specific examples of the certification processing will be described with reference to FIGS. 7 and 8.

[Fourth Certification Processing Example]

Figure 7:
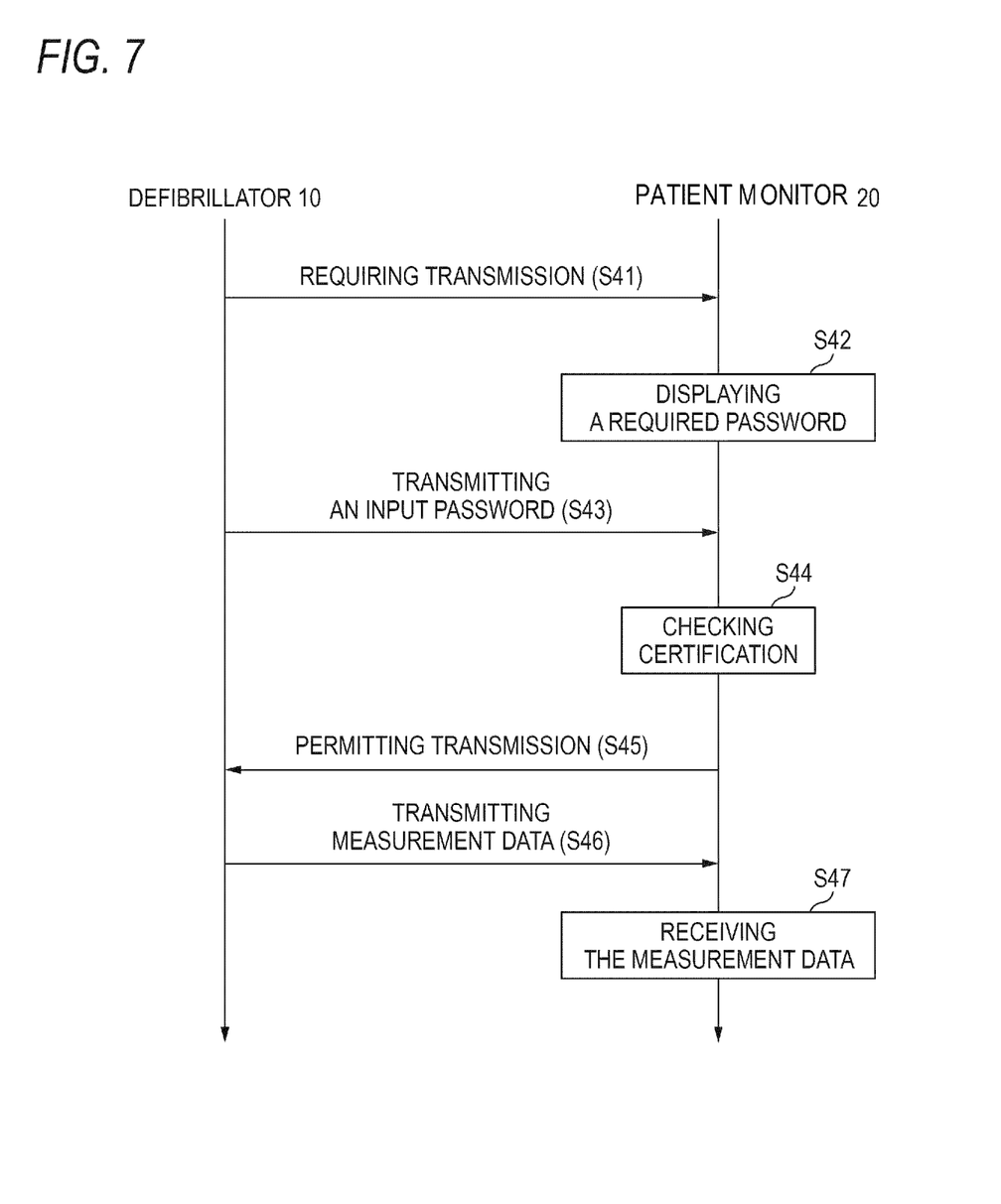
FIG. 7 is a timing chart showing a fourth certification processing example between the defibrillator 10 and the patient monitor 20 according to the present invention.

FIG. 7 is a timing chart showing a fourth certification processing example (continued from the embodiment 1) between the defibrillator 10 and the patient monitor 20 according to the present embodiment.

Prior to transmission of measurement data, a communication unit 14 in the defibrillator 10 transmits a transmission demand to the patient monitor 20 (S41). A communication unit 23 in the patient monitor 20 receives the transmission demand (S41). Then, the certification unit 26 in the patient monitor 20 creates a required password and displays the required password on a display unit 22 (S42).

A user of the defibrillator 10 inputs a password while referring to the required password displayed on the patient monitor 20. The communication unit 14 transmits the input password to the patient monitor 20 (S43).

The communication unit 23 of the patient monitor 20 receives the input password (S43). Also, the certification unit 26 decides whether or not the input password corresponds to the required password (S44). If the input password corresponds to the required password, the certification unit 26 transmits a transmission permission to the defibrillator 10 through the communication unit 23 (S45).

The communication unit 14 receives the transmission permission (S45). After receiving the transmission permission, the communication unit 14 reads measurement data from a storage unit 13 and then transmits the measurement data to the patient monitor 20 (S46). The communication unit 23 receives the measurement data transmitted from the defibrillator 10 (S46). The communication unit 23 displays the received measurement data on the display unit 22 (S47).

[Fifth Certification Processing Example]

Figure 8:
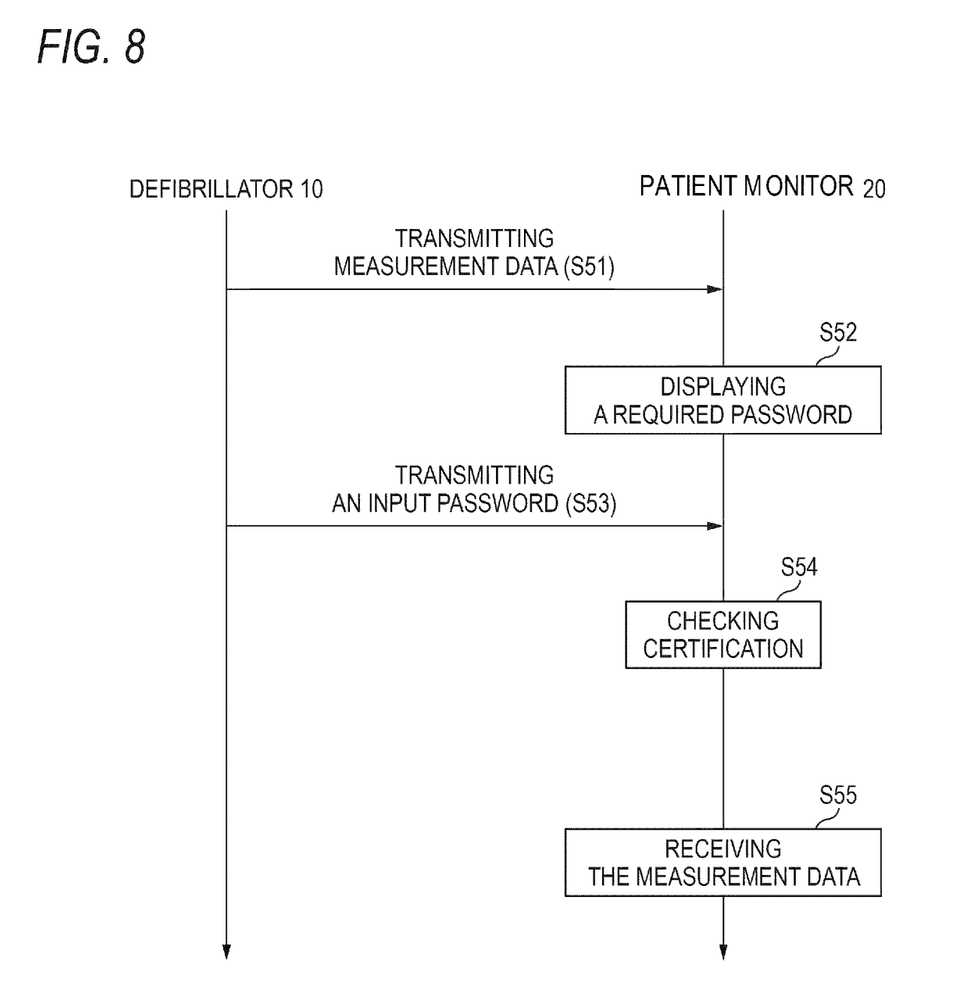
FIG. 8 is a timing chart showing a fifth certification processing example between the defibrillator 10 and the patient monitor 20 according to the present invention.

Next, a fifth certification processing example (continued from the embodiment 1) of the medical device system according to the embodiment 2 will be described. FIG. 8 is a timing chart showing the fifth certification processing example between a defibrillator 10 and a patient monitor 20 according to the present embodiment.

On the basis of a certain trigger (e.g., pressing of a transmission button provided on the defibrillator 10), the communication unit 14 of the defibrillator 10 transmits measurement data to the patient monitor 20 (S51). Also, the certification unit 26 of the patient monitor 20 creates a required password after receiving the measurement data, and then displays the required password on the display unit 22 (S52).

A user (e.g., a nurse), who is to perform operation for data transfer between the defibrillator 10 and the patient monitor 20, inputs a password corresponding to the required password through an input unit 15 of the defibrillator 10 while referring to the required password displayed on the patient monitor 20. The communication unit 14 transmits the input password to the patient monitor 20 (S53).

The communication unit 23 receives the input password transmitted from the defibrillator 10 (S53). The certification unit 26 decides whether or not the received input password corresponds to the required password (S54). If two passwords do not correspond to each other, the communication unit 23 deletes the measurement data received form the defibrillator 10. On the other hand, if two passwords correspond to each other, the patient monitor 20 displays the received measurement data on the display unit 22 (S55).

Next, the effects of the medical device system 1 of the present invention will be described. In the first to fifth certification processings as described above, the patient monitor 20 receives and uses measurement data acquired by the defibrillator 10, only if certification between the defibrillator 10 and the patient monitor 20 succeeds. By performing such certification processings, data transfer between correct devices can be ensured. Because data transfer between correct devices can be realized, unintended transmission and reception of measurement data can be avoided. Thus, a risk, such as confusing data of patients, can be reduced.

Also, the patient monitor 20, by which measurement data is received, displays the measurement data measured by the defibrillator 10 and the measurement data measured by the patient monitor 20 side by side in time series (FIG. 3). Thus, a user can treat a patient while referring to a state of the patient during a period of time during which the patient was treated by the defibrillator 10. For example, when treating a patient who comes by an ambulance, doctors or nurses can treat the patient while visually referring to both of measurement data of vital signs measured in the ambulance and measurement data of the current vital signs.

Also, the communication unit 14 and the communication unit 23 are contemplated to perform communication processing based on short-distance wireless communication standards, including Bluetooth (registered trademark). Thus, the defibrillator 10 communicates with the patient monitor 20 at a physically close distance. As the physical distance becomes close, a user can input the input password while precisely referring to the required password. Accordingly, a case where a transmission destination is incorrectly inputted can be avoided.

Next, the first to fifth certification processing examples (FIGS. 2, 4, 5, 7 and 8) as described above will be considered. When the defibrillator 10 transmits measurement data after it is decided that certification succeeds (first, second and fourth certification processing examples), the patient monitor 20 cannot refer to the measurement data until certification succeeds. Thus, data of a patient is hidden in the defibrillator 10 until a transmission source and a transmission destination are confirmed by certification, and this is preferable in terms of management of personal information.

Also, in the first certification processing example, the defibrillator 20 performs creation of the required password and certification processing, and the patient monitor 20 performs only displaying processing of the required password. Accordingly, the need of changing in design of the patient monitor 20 or the like is not caused, and thus the existing patient monitor 20 can be substantially intactly used to implement the certification as described above.

In the foregoing, the invention achieved by the present inventors has been described in detail based on the embodiments thereof, but it will be appreciated that the present invention is not limited to the above mentioned embodiments and various modifications thereof can be made without departing from the spirit thereof.

For example, although in the foregoing description, the case where data is transmitted from the defibrillator 10 to the patient monitor 20 is described, the present invention is not necessarily limited thereto. The present invention can be applied to transfer data between any measuring devices of the medical field, and for example, can be also applied to transfer data between patient monitors. Also, it will be appreciated that the present invention can be applied to other types of medical devices, such as an electrocardiogram measuring device.

Also, although in the foregoing description, the patient monitor 20 is used to display the received measurement data, the measurement data may be used in analyzing states of a patient or the like.

The first medical device and the second medical device are configured to perform data transfer after certification processing is performed. By performing the certification processing, a data transfer between correct devices can be ensured. Because a data transfer between correct devices can be realized, problems, such as confusingly handling data of patients, can be avoided.

The present invention can provide a medical device system and a medical device, in which a correct transmission and reception of measurement data can be performed between correct devices.

What is claimed is:

1. A medical device system comprising a first medical device and a second medical device, wherein the first medical devices includes:

a certification unit that creates a required password, which is a password required to be inputted;

a first measuring unit that acquires first measurement data of at least one kind of vital signs of a patient;

a first display unit that displays the first measurement data;

a first storage unit that stores the first measurement data; and a first communication unit that transmits the required password to the second medical device, and that transmits the first measurement data from the first storage unit to the second medical device, wherein the second medical device includes:
a second communication unit that receives the required password from the first communication unit, and that receives the first measurement data from the first communication unit;
a second measuring unit that acquires second measurement data of the at least one kind of vital signs of the patient; and
a second display unit that displays the required password, and that displays the first measurement data received from the first medical device and the second measurement data acquired by the second measuring unit,
wherein the first measurement data is permitted to be used in the second medical device where certification in view of the required password succeeds, and
wherein the first measurement data of the at least one kind of vital signs of the patient and the second measurement data of the at least one kind of vital signs of the patient are displayed side by side in a direction of a time axis.

2. The medical device system according to claim 1,
wherein the first display unit displays the required password,
wherein the certification unit decides that the certification processing succeeds when an input password inputted from a user to the first medical device corresponds to the required password; and
wherein the first communication unit transmits the first measurement data acquired by the first measuring unit to the second medical device after the certification unit decides that certification succeeds.

3. The medical device system according to claim 1, wherein the first communication unit and the second communication unit perform communication processing based on a short-distance wireless communication standard.

4. The medical device system according to claim 1, wherein the second display unit displays first waveforms of the first measurement data and second waveforms of the second measurement data along the time axis.

5. The medical device system according to claim 1, wherein the first communication unit and the second communication unit communicate with each other based on short-distance wireless communication standards.

6. A medical device that:
receives a required password, which is a password required to be inputted and is created by a certification unit of an opposing device;
displays the required password;
receives first measurement data of at least one kind of vital signs of a patient measured by the opposing device to be used in the medical device itself when a certification processing between the medical device and the opposing device succeeds;
acquires second measurement data of the at least one kind of vital signs of the patient; and
displays the first measurement data received from the opposing device and the second measurement data,
wherein the first measurement data of the at least one kind of vital signs of the patient and the second measurement data of the at least one kind of vital signs of the patient are displayed side by side in a direction of a time axis.

7. A medical device comprising:
a measuring unit that acquires first measurement data of the at least one kind of vital signs of a patient;
a certification unit that creates a required password, which is a password required to be inputted;
a display unit that displays the first measurement data;
a storage unit that stores the first measurement data; and
a communication unit that transmits the required password to an opposing device which is a data transmission destination, and that transmits the first measurement data from the-storage unit to the opposing device, after certification processing between the medical device and the opposing device succeeds,
wherein the opposing device receives the required password from the communication unit and displays the required password, and
wherein, in the opposing device, the first measurement data received by the opposing device and second measurement data of the at least one kind of vital signs of the patient acquired by the opposing device are displayed side by side in a direction of a time axis.

* * * * *